United States Patent
Baym et al.

(10) Patent No.: US 8,702,614 B2
(45) Date of Patent: Apr. 22, 2014

(54) INFLATABLE CUFF WITH BUILT-IN DRUG DELIVERY DEVICE FOR DYNAMIC DRUG THERAPY RESPONSE TO BLOOD PRESSURE INCIDENTS

(75) Inventors: Michael H. Baym, Cambridge, MA (US); Edward S. Boyden, Chestnut Hill, MA (US); Roderick A. Hyde, Redmond, WA (US); Jordin T. Kare, Seattle, WA (US); Eric C. Leuthardt, St. Louis, MO (US); Nathan P. Myhrvold, Bellevue, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 8 days.

(21) Appl. No.: 13/373,364

(22) Filed: Nov. 8, 2011

(65) Prior Publication Data

US 2013/0116615 A1 May 9, 2013

(51) Int. Cl.
*A61B 5/02* (2006.01)
*A61M 31/00* (2006.01)

(52) U.S. Cl.
USPC .............. 600/490; 600/493; 604/66; 604/503

(58) Field of Classification Search
USPC ............. 604/65–67, 173, 180, 304, 305, 307, 604/308; 600/490–499
See application file for complete search history.

(56) References Cited

U.S. PATENT DOCUMENTS

| | | | |
|---|---|---|---|
| 4,080,966 A | 3/1978 | McNally et al. | |
| 4,280,494 A | 7/1981 | Cosgrove, Jr. et al. | |
| 4,796,184 A | 1/1989 | Bahr et al. | |
| 5,527,288 A | 6/1996 | Gross et al. | |
| 5,848,991 A | 12/1998 | Gross et al. | |
| 5,997,501 A | 12/1999 | Gross et al. | |
| 6,251,080 B1 * | 6/2001 | Henkin et al. | 600/490 |
| 6,723,077 B2 | 4/2004 | Pickup et al. | |
| 7,267,665 B2 * | 9/2007 | Steil et al. | 604/131 |
| 7,392,080 B2 * | 6/2008 | Eppstein et al. | 604/20 |
| 7,481,772 B2 | 1/2009 | Banet | |
| 7,544,190 B2 | 6/2009 | Pickup et al. | |
| 7,717,855 B2 | 5/2010 | Caldarone et al. | |
| 8,182,429 B2 * | 5/2012 | Mason | 600/485 |
| 8,319,401 B2 | 11/2012 | Mckenna | |
| 2002/0016610 A1 | 2/2002 | Hovanes et al. | |
| 2002/0017296 A1 | 2/2002 | Hickle | |
| 2002/0042635 A1 | 4/2002 | Zhang et al. | |
| 2003/0004403 A1 | 1/2003 | Drinan et al. | |
| 2003/0065294 A1 | 4/2003 | Pickup et al. | |
| 2004/0087916 A1 | 5/2004 | Pickup et al. | |
| 2004/0167409 A1 | 8/2004 | Lo et al. | |
| 2004/0181196 A1 | 9/2004 | Pickup et al. | |
| 2005/0148882 A1 | 7/2005 | Banet et al. | |
| 2005/0182389 A1 | 8/2005 | LaPorte et al. | |

(Continued)

OTHER PUBLICATIONS

PCT International Search Report; International App. No. PCT/US12/64071; Jan. 17, 2013; pp. 1-2 (including 6 pages of the Search Report).

(Continued)

*Primary Examiner* — Nicholas Lucchesi
*Assistant Examiner* — Leah Stohr

(57) ABSTRACT

An inflatable cuff in a blood pressure-measurement system is integrated with a drug delivery device. The drug delivery device is configured to automatically deliver a drug dermally or transdermally to the individual in response to the measured blood pressures.

40 Claims, 7 Drawing Sheets

(56) References Cited

U.S. PATENT DOCUMENTS

| | | |
|---|---|---|
| 2005/0187485 A1 | 8/2005 | Fumuro et al. |
| 2005/0288597 A1 | 12/2005 | Kishimoto et al. |
| 2006/0100530 A1 | 5/2006 | Kliot et al. |
| 2006/0217617 A1 | 9/2006 | Wachtenberg |
| 2006/0253041 A1 | 11/2006 | Shin et al. |
| 2007/0191702 A1* | 8/2007 | Yodfat et al. ............... 600/365 |
| 2007/0265533 A1 | 11/2007 | Tran |
| 2009/0076349 A1 | 3/2009 | Libbus et al. |
| 2009/0187167 A1 | 7/2009 | Sexton et al. |
| 2011/0264028 A1 | 10/2011 | Ramdas et al. |
| 2013/0211267 A1 | 8/2013 | Wang et al. |

OTHER PUBLICATIONS

PCT International Search Report; Application No. PCT/US 12/64080; Jan. 25, 2013; pp. 1-2.

"Hypertension"; Wikipedia, the free encyclopedia; printed on Nov. 7, 2011; pp. 1-22.

"Systolic Hypertension"; Wikipedia, the free encyclopedia; printed on Nov. 7, 2011; pp. 1-4.

* cited by examiner

510
Provide a blood pressure monitoring unit having a built-in ultrasound sensor and a drug delivery device, wherein the unit is attachable to an individual

520
Make one or more blood pressure measurements of the individual with the ultrasound sensor in the attached unit

530
Use the attached drug-delivery device to dispense a drug to the individual in response to the measured blood pressure measurements as prescribed

610
Provide a drug-delivery skin patch having a structurally integrated or built-in blood pressure sensor (610), wherein the skin patch is adapted to be attached to a skin portion of an individual.

---

620
configure the skin patch to needle-lessly deliver a drug dermally or transdermally to the individual as may be prescribed or appropriate in response to blood pressure determinations with the built-in blood pressure sensor

INFLATABLE CUFF WITH BUILT-IN DRUG DELIVERY DEVICE FOR DYNAMIC DRUG THERAPY RESPONSE TO BLOOD PRESSURE INCIDENTS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation of U.S. patent application Ser. No. 13/373,365, entitled SYSTEMS AND METHODS FOR DYNAMIC DRUG THERAPY RESPONSE TO BLOOD PRESSURE INCIDENTS, naming Michael H. Baym; Edward S. Boyden; Roderick A. Hyde; Jordin T. Kare; Eric C. Leuthardt; Nathan P. Myhrvold; and Lowell L. Wood, Jr. as inventors, filed on Nov. 8, 2011, which is currently co-pending, or is an application of which a currently co-pending application entitled to the benefit of the filing date.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

BACKGROUND

The present application relates, in general, to antihypertensive drug therapy. In particular, the application relates to controlling hypertension episodes round the clock.

Hypertension is an inevitable disease of all populations in their second half-century of life, no matter who-or-where they may be. Moreover, hypertension assertedly creeps-up linearly with time, and soon enough becomes the major cause of morbidity and mortality. Severe hypertension insidiously damages the central nervous system—even in a victim barely into his or her second half-century. See e.g., New England Journal of Medicine.

Increased blood pressures are associated with increased chances of having a stroke, heart attack, kidney failure or heart failure and a whole host of other maladies or health complications. Medical classification of hypertension is based on blood pressure ranges. An exemplary blood pressure classification in common use is as follows:

| Blood Pressure Classification Table | | |
|---|---|---|
| 115 | 75 | Desireable |
| 120-139 | 80-89 | Prehypertension |
| 140-159 | 90-99 | Hypertension Stage 1 |
| 160 or over | 100 or over | Hypertension Stage 2 |

As the blood pressures rise above 115/75 there is an increased incidence of the above-mentioned complications. This increased incidence worsens as the blood pressure increases above 115/75 (i.e., mean arterial pressures above 95 mm Hg) are linearly bad. Deterioration of the vascular beds of several heavily vascularized vital organs (e.g., kidneys, heart and brain) appears to be linear with the time-integral of mean arterial pressure above a desirable threshold of 95 mm Hg. On top of general vascular bed-rot, macro problems such as various flavors of myocardial 'remodeling', heart failure, etc. occur.

A problem with current diagnosis and treatment of hypertension is that they are usually based on only an individual or few measurements of blood pressure without taking into account of hypertensive episodes or excursions that may contribute to a higher time-integral of mean arterial pressure above the desirable threshold of 95 mm Hg. See e.g., Powers B, et al "Measuring blood pressure for decision making and quality reporting: where and how many measures?" Ann Intern Med 2011; 154: 781-788, and Appel L, et al "Improving the measurement of blood pressure: Is it time for regulated standards?" Aim Intern Med 2011; 154: 838-839. Both of these references and all other references cited in this disclosure are incorporated by reference herein in their entireties.

Consideration is now given to ways to promptly treat blood pressure increases in an individual toward reducing the time-integral of mean arterial pressure above a desirable threshold of 95 mm Hg.

SUMMARY

Systems and methods are provided for treating blood pressure excursions in an individual. The systems and methods rely on real or near real time measurement of any blood pressure excursions in an individual and prompt drug therapy to address the blood pressure excursions.

The systems and methods involve automatically detecting when hypertension has commenced in an individual, and to promptly medicating so as to robustly suppress it. The automatic detection of is based on use of suitable sensors attached to the individual to non-invasively monitor blood pressure over extended periods of time. A sensor-informed controlled drug delivery system dispenses a physician-specified dosing of at-least-one hypertension medication into the body of the individual to maintain blood pressure(s) below physician-specified level(s).

The systems and methods provide means of hypertension-suppression to everyone in a real-time monitored-&-adjusted manner, so as to accommodate individual needs and life demands. The systems and methods provide quasi-real-time coupling between blood pressure measurement and medication in order to provide low-latency, high-authority negative feedback as blood pressure can fluctuate greatly over a timescale of a few hours.

BRIEF DESCRIPTION OF THE FIGURES

In the accompanying drawings:

FIG. 5 is a flow diagram illustrating exemplary method for dynamically treating hypertension or other blood pressure incidents, in accordance with the principles of the solutions described herein;

FIG. 6 is a flow diagram illustrating exemplary method for dynamically treating hypertension or other blood pressure incidents, in accordance with the principles of the solutions described herein.

Throughout the figures, unless otherwise stated, the same reference numerals and characters are used to denote like features, elements, components, or portions of the illustrated embodiments.

DESCRIPTION

In the following description of exemplary embodiments, reference is made to the accompanying drawings, which form a part hereof. It will be understood that embodiments described herein are exemplary, but are not meant to be limiting. Further, it will be appreciated that the solutions described herein can be practiced or implemented by other than the described embodiments. Modified embodiments or alternate embodiments may be utilized, in the spirit and scope of the solutions described herein.

One approach is directed to automated monitoring of blood pressures and real time or near real time drug therapy upon indications of hypertension or other excursions in blood pressure values.

Figure 1:
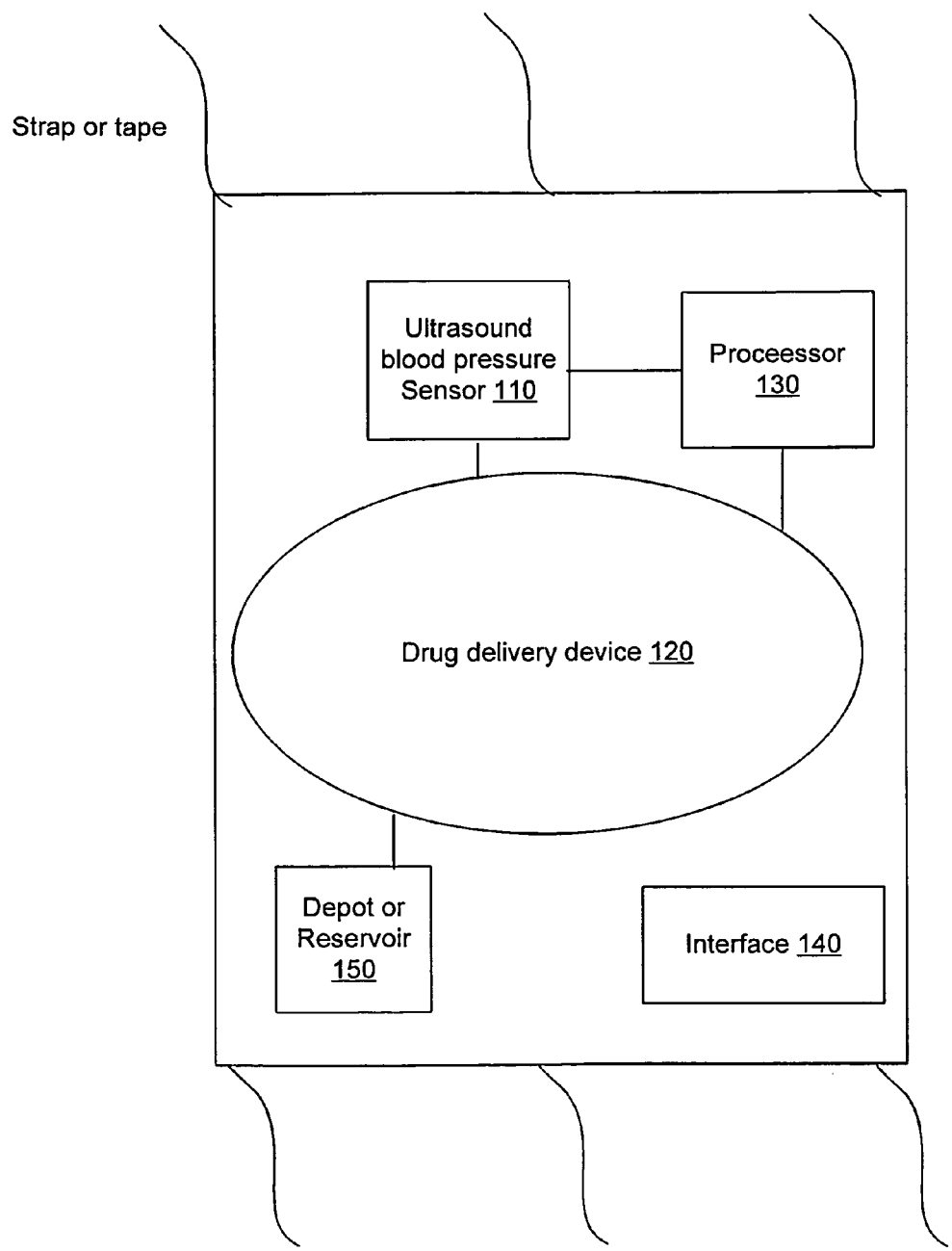
FIG. 1 is a block diagram illustrating components of an exemplary device for dynamically suppressing hypertension, in accordance with the principles of the solutions described herein.

FIG. 1 shows and exemplary device 100 for automated monitoring of blood pressures and real time or near real time drug therapy of hypertension. Device 100 includes a blood pressure sensor 110 coupled to a drug-delivery device 120. The two are integrated together as a unit attachable to the individual (e.g., using straps or adhesive). Device 100 may be adapted to be attached to a skin portion of the individual and/or fully or partially implanted in the individual. Device 100 may include a processing circuit 130 configured to process blood pressure data and other data. Processing circuit 130 may include a memory to store one or more measured blood pressure values. Processing circuit 130 may also include a microprocessor programmed to execute drug-dispensing instructions based on blood pressure values.

Further, device 120 may include an input/output communications interface 140 that may, for example, be used to communicate blood pressure values, device actions and/or device status to, or receive data or instructions from an external point via the input/output communications interface. Processing circuit 130/interface 140 may be configured to receive parameters relating drug dispensation requirements and blood pressure values, and/or other instructions from an external source.

Blood pressure sensor 110 is configured to make one or more ultrasonic measurements of an individual's blood pressure. Blood pressure sensor 110 may be battery powered. Blood pressure sensor 110 may be any suitable ultrasonic transducer that provides fast, accurate blood pressure readings. Sensor 110 may, for example, be a piezo electric transducer (such as of the type sold under the name Arterial Pressure Transducer by MTC ElectroCeramics, 232 Forbes Road, Bedford, Ohio 44146-5418 USA) or a thin film transducer (such as of the type described by Tsubai M., et al. "Development of an Ultrasonic Probe with Measurement of Contact Pressure Distribution," SICE-ICASE, 2006. International Joint Conference, 18-21 Oct. 2006, pp. 3827-3830). Sensor 110 may be a Doppler ultrasound device that allows both blood flow and blood pressure to be measured. See e.g., Kazamias et al. "Blood pressure measurement with Doppler ultrasonic flowmeter," J Appl Physiol 1971; 30:585-588. and "Toward Noninvasive Blood Pressure Assessment in Arteries by Using Ultrasound, Ultrasound in Medicine & Biology," Volume 37, Issue 5, May 2011, pages 788-797.

In general, ultrasound sensor 110 may be one of a broad angle ultrasound sensor, a directed beam ultrasound sensor, a bistatic ultrasound sensor and a phased array ultrasound sensor. In a version of device 100, sensor 110 may be configured to make Doppler measurements of a blood flow in the individual by correlating blood velocity and pressure. Sensor 110 may be configured to locate a blood vessel and make one or measurements of blood pressure in the located blood vessel. Further, sensor 110 may be configured to measure dynamic changes in a blood vessel size or elasticity that are indicative of the blood pressure. Sensor 110 may be configured to apply sufficient energy to jostle blood in a blood vessel or walls of the blood vessel and to measure the blood pressure response to the applied energy.

Drug delivery device 120, which is responsive to sensor 110 is configured to dispense or apply a drug to the individual in response to the measured blood pressure. In general, drug delivery device 120 may configured to dispense or apply a drug to the individual in response to current, average and/or cumulative blood pressure values. In a version of device 100, drug delivery device 120 is configured to dispense the drug in response to changes in blood pressure values and/or in projected blood pressure values. Drug delivery device 120 may be configured to dispense the drug in response to parameters or characteristics of the blood pressure profile including pulse shape, and/or systolic/diastolic blood pressure values. Drug-delivery device 120 may include one or one or more needles and/or, microjets for delivery of the drug to the individual. Alternately or additionally, drug-delivery device 120 may be configured to use iontophoresis and/or sonophoresis for delivery of the drug to the individual.

Drug delivery device 120 may include or supplied by a drug reservoir 150. Drug reservoir may be disposed ex-vivo or in-vivo (e.g., sub-dermal or buccal). The drug may be delivered, for example, into the gastrointestinal tract or the vasculature of the individual to suppress the hypertensive excursions and toward maintaining blood pressure(s) in physician-specified ranges. The dispensed drug may be any suitable drug or combination of drugs that are prescribed for treatment of blood pressure conditions. Common drugs prescribed treatment of blood pressure conditions include, for example, diuretics, angiotensin converting enzyme (ACE) inhibitors, angiotensin II receptor blockers (ARBs), beta blockers, calcium channel blockers (CCBs), blood vessel dilators, alpha blockers and nervous system inhibitors. Medical quantities of interest for several pertinent medications may be in the range of a few mg to a few dozen mg daily. Thus a modest capacity of reservoir 150 may readily suffice for multi-month intervals between refilling. Drug delivery device 120 may be configured to dispense the drug to dynamically regulate the individual's blood pressure. The dispensed drug may be intended to lower or raise the individual's blood pressure, and/or to reach or maintain a target blood pressure or range. Alternatively or additionally, the dispensed drug may be intended to treat a condition sensitive to a result and/or effect of the individual's blood pressure.

A further version of device 120 may include an altitude-sensing device (e.g., an accelerometer) configured to determine an altitude of blood pressure sensor 110. Device 100 may use processing circuitry 130 or other circuits to correct a blood pressure measurement for a relative height or altitude of blood pressure sensor 110. For example, device 100 may be configured to distinguish blood pressures measurements made when the individual is sitting form those made when the individual is standing.

Figure 2:
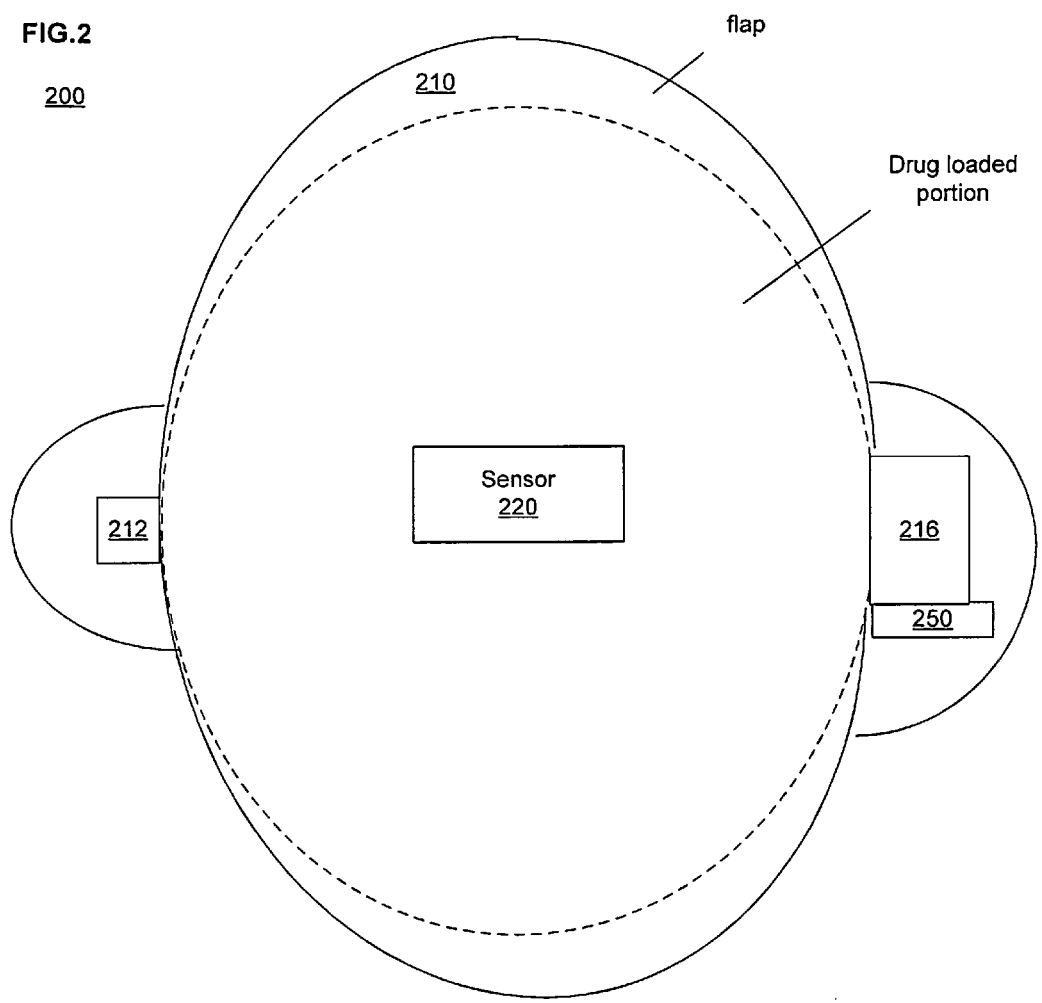
FIG. 2 is a block diagram illustrating a drug-delivery skin patch with a built-in blood pressure measurement sensor, in accordance with the principles of the solutions described herein.

FIG. 2. shows an exemplary system 200 utilizing a skin patch 210 to deliver drugs for real or near real-time treatment of hypertension or other blood pressure excursions in an individual. Skin patch 210 has a blood pressure sensor 220 structurally integrated therein. The integrated structure 210/220 is configured to be attached to a skin portion of an individual. Blood pressure sensor 220 is configured to determine a blood pressure of the individual and skin patch 210 is configured to needle-lessly deliver a drug dermally or transdermally to the individual in response to the determined blood pressure.

Blood pressure sensor 220, which is integrated with skin patch 210, may be any suitable type of device for measuring blood pressure. For example, blood pressure sensor 220 may be a mechanical, optical, and/or electric sensor. Blood pressure sensor 220, like sensor 110, may be an ultrasonic sensor (e.g., a broad angle, a directed, a bistatic sensor, or a phased array ultrasound sensor). Blood pressure sensor 220 may be battery powered.

Blood pressure sensor 220 may be configured to locate a blood vessel in the vicinity of the applied skin patch and make one or measurements of blood pressure in the located blood vessel. Blood pressure sensor 220 may be further configured to measure a blood pressure response to applied energy he blood pressure sensor may be configured to apply sufficient energy to jostle blood in a blood vessel or the blood vessel itself. Blood pressure sensor 220 may be configured to measure dynamic changes in a blood vessel size or elasticity that are indicative of the blood pressure. Blood pressure sensor 220 may be configured to make Doppler measurements of a blood flow in the individual by correlating blood velocity and pressure. Skin patch 210 may include a microprocessor 216 for processing blood pressure data and drug-delivery instructions.

Skin patch 210 may include suitable electrical circuits to deliver the drug to the individual using iontophoresis and/or electroporation. Alternatively or additionally, skin patch 210 may include suitable electronic or mechanical drivers to deliver the drug using iontophoresis, sonophoresis, microjets, and/or needle-less injection. The electrical circuits/drivers may be configured to deliver the drug in response to current, average and/or cumulative blood pressure values, in response to trends in blood pressure values and/or to projected blood pressure values, and/or in response to parameters or characteristics of the blood pressure profile including pulse shape, and/or systolic/diastolic blood pressure values.

A version of skin patch 210 may include an input/output communications interface 250 for communicating blood pressure values, system actions and/or system status with an external point via the input/output communications interface.

A further version of system 200 may include an altitude-sensing device 212 (e.g., an accelerometer configured to determine an altitude of blood pressure sensor 220. Skin patch 210 may include suitable processing circuitry to correct a blood pressure measurement for a relative height or altitude of blood pressure sensor 220. For example, system 200 may be configured to distinguish blood pressures measurements made when the individual' arm is lowered (e.g., while sitting) from those made when the arm is raised or higher while standing.

System 200 may be configured so that skin patch 210 delivers the drug to dynamically regulate the individual's blood pressure. The type and amount of drug dispensed may be to lower or raise the individual's blood pressure, or reach or maintain a target blood pressure or range. Skin patch 210 may additionally or alternatively deliver a drug to treat a condition sensitive to a result and/or effect of the individual's blood pressure.

Figure 3:
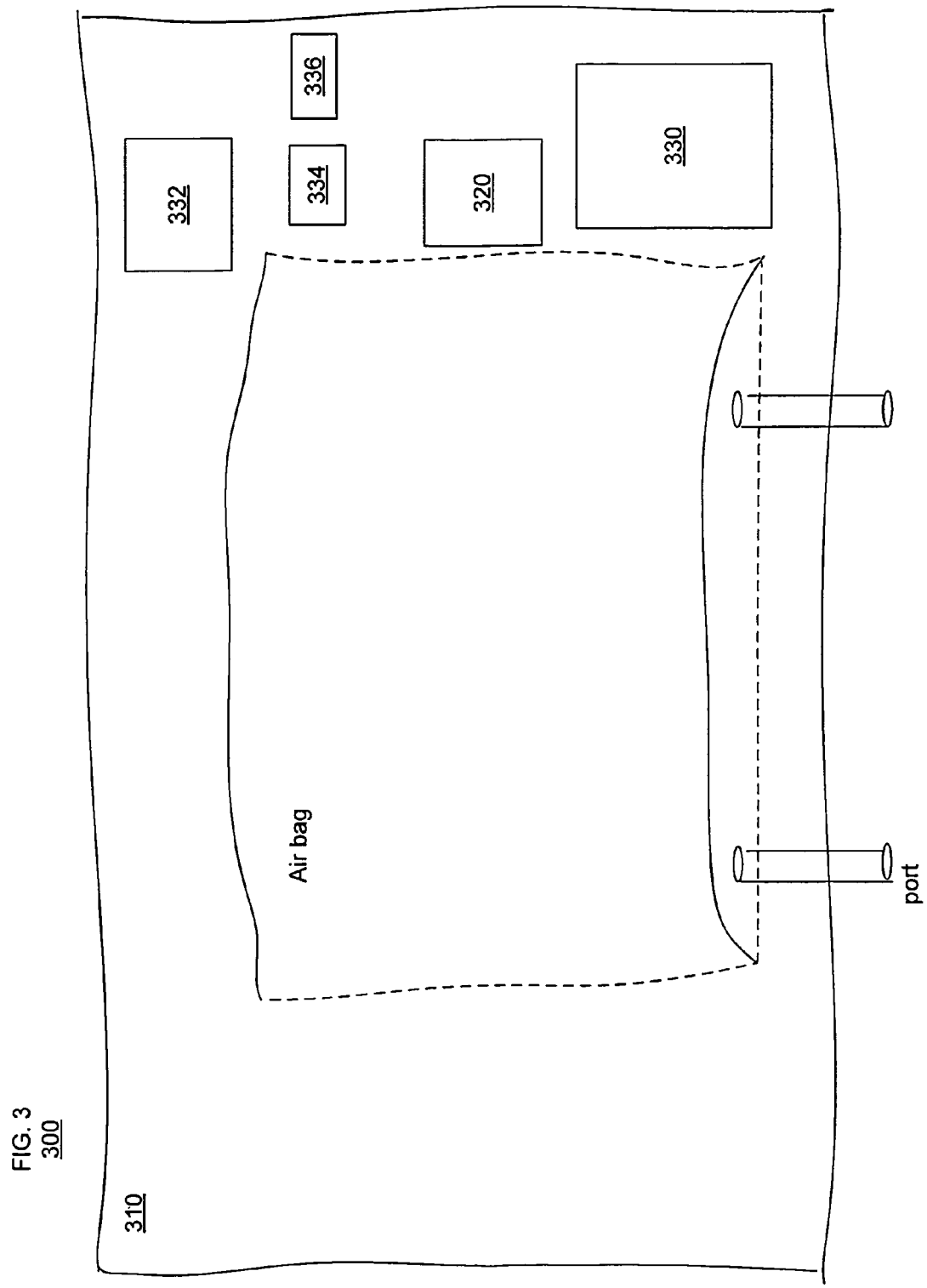
FIG. 3 is a block diagram illustrating a blood pressure-measurement system having an inflatable cuff with a built in automated drug delivery device, in accordance with the principles of the solutions described herein.

FIG. 3 shows another exemplary blood pressure measurement and treatment system 300, system 300 includes an inflatable cuff 310, a pressure-measuring device 320 and a drug-delivery device 330 that is integrated or built into inflatable cuff 310.

Inflatable cuff 310 generally has the same or similar construction as inflatable cuffs that are commonly used in conventional home, clinic or doctor's office blood pressure measurement systems. See e.g. Thede, Roger C. U.S. Pat. No. 6,932,773 Wrist type blood pressure meter cuff; Itonaga, Kazunobu et al. U.S. Pat. No. 6,336,901 Sphygmomanometer cuff achieving precise measurement of blood pressure; Sionell Goran U.S. Pat. No. 4,572,205 Method at blood pressure measurement and a blood pressure cuff for carrying out the method; Nishibayashi, Hideo U.S. Pat. No. 6,969,356 Inflatable cuff for blood pressure measurement; Knoblich, Stanley M. U.S. Pat. No. 5,069,219 Self snugging universal blood pressure cuff; Williams U.S. Pat. No. 4,117,835 Method and apparatus for blood pressure measurements; Gorelick, Donald E. U.S. Pat. No. 4,116,230 Blood pressure cuff automatic deflation device; Speidel, Blasius U.S. Pat. No. 4,116,217 Deflation valve for blood pressure measuring devices; Affeldt, et al. U.S. Pat. No. 4,112,929 Method for measuring the blood pressure of a patient; Keller U.S. Pat. No. 4,109,646 Automatic blood pressure cuff applicator; Aldridge, et al. U.S. Pat. No. 4,108,310 Blood pressure testing kit; Ueda U.S. Pat. No. 4,106,499 Sphygmomanometer cuff; and Williams et al. U.S. Pat. No. 4,105,021 Method and arrangement for measuring blood pressure. All of the foregoing patents and other references cited in this disclosure are incorporated by reference in their entireties herein.

Figure 4:
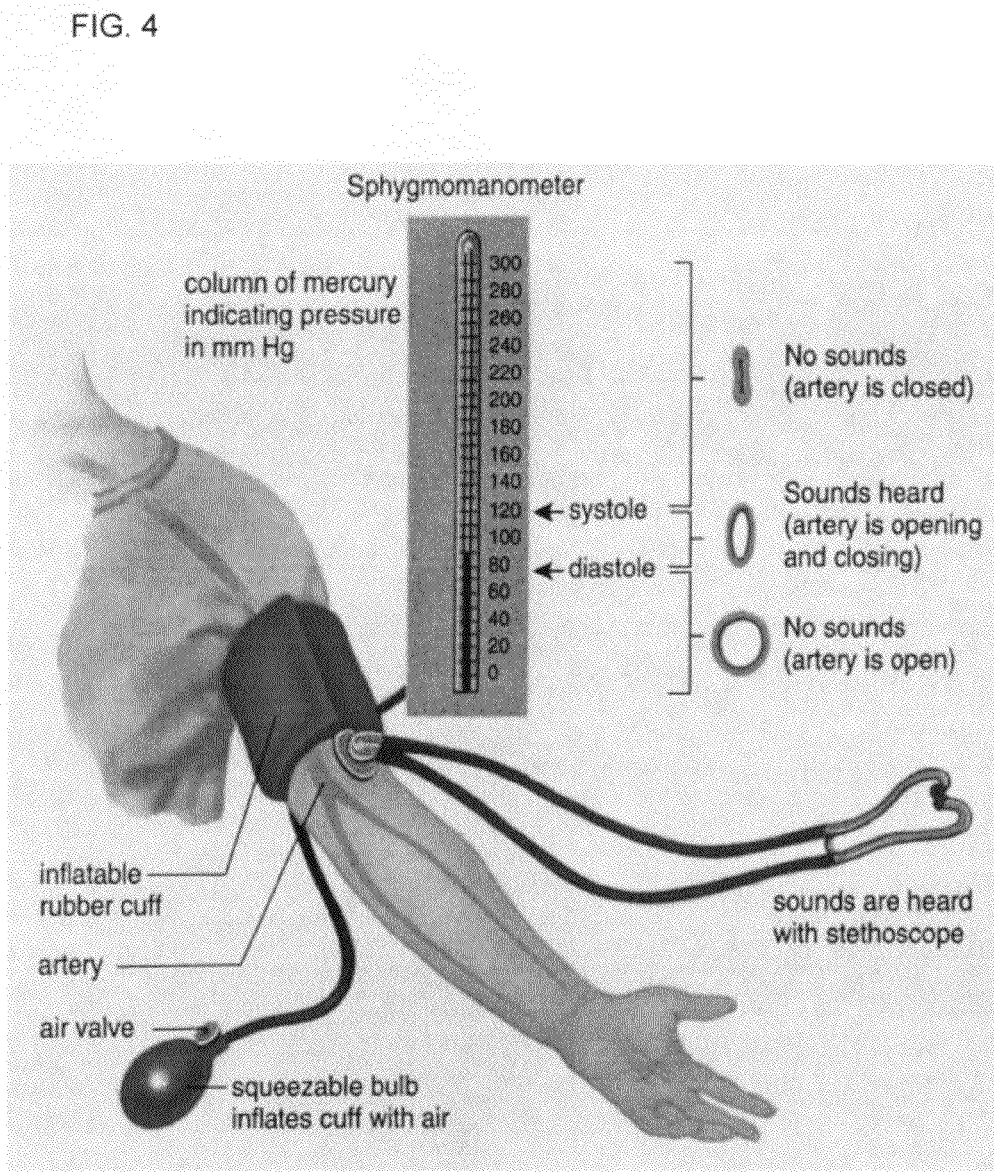
FIG. 4 is an illustration of the auscultatory method of measuring blood pressure that has been traditionally deployed in doctors' offices and clinics for over a century.

In system 300, inflatable cuff 310 like conventional blood pressure measurement cuffs includes a flexible tape, band or strip 312 that can be wrapped and secured around an individual's limb (e.g. arm, leg or finger). An inflatable bag or bladder 314 made of the same or other materials is built into tape, band or strip 312. When blood pressure is measured, cuff 310 is inflated, automatically or manually, to constrict an artery so that no blood flows through. Since the pressure in the cuff is greater than the pressure in the artery, the artery is closed off and no blood flows through. As the cuff pressure is gradually released, but the artery is still partially constricted, blood flow resumes. In the auscultatory method of measuring blood pressure that has been traditionally deployed in doctors' offices and clinics, the sounds can be heard with a stethoscope because the blood flows turbulently, causing audible sounds. When enough cuff pressure is released to fully open the artery, the blood flows freely and the sounds disappear because smooth flowing blood does not create sounds. (See FIG. 4). As the cuff is deflated and blood flow resumes through the partially constricted artery, the first sounds correspond to systolic pressure and the end of sounds correspond to diastolic pressure.

Automated or electronic oscillometric blood pressure monitors do not rely on sound detection but instead depend on analysis of pressure pulses or waves. They measure mean arterial pressure (MAP) and use oscillometric detection to calculate systolic and diastolic values. When the cuff starts to deflate, blood resumes flowing, causing the artery walls to vibrate. The cuff senses these vibrations and a blood pressure meter recognizes this as the systolic pressure. When the blood resumes normal flow, vibrations cease. The blood pressure meter recognizes this as the diastolic pressure. Other methods, for example, include ultrasound (used mainly to detect systolic pressure) and the finger cuff method of Penaz, which can record beat-to-beat arterial pressure noninvasively from the finger. See e.g., Booth, J (1977). "A short history of blood pressure measurement". Proceedings of the Royal Society of Medicine 70 (11): 793-9.

In system 300, inflatable cuff 310 is coupled to a suitable electronic blood pressure measuring device 320 for measuring or deriving blood pressures from physical changes (i.e., arterial constriction and deconstriction) resulting from the inflation/deflation of cuff 310. Device 320 may utilize any suitable non invasive technique to measure or derive blood pressure values. The suitable technique may, for example, be based on mechanical, audio, ultrasound, or optical detection of cuff pressure responses and behaviors. Correspondingly, device 320 may include suitable mechanical, audio, ultrasound, optical, and/or electric sensors and processors. The technique utilized may involve actual pressure measurements or microprocessor analysis of pressure oscillations or waves. Further, the measured or derived blood pressure values may correspond to the systolic pressure or diastolic pressure, mean arterial pressure or any other indicia of blood pressure behavior of the individual. For convenience in description, all of these measured or derived blood pressure values may be referred to herein as "the measured pressure(s) corresponding to the individual's diastolic and/or systolic blood pressures."

With renewed reference to FIG. 3, system 300 further includes drug-delivery device 330 integrated with inflatable cuff 310 and coupled to electronic blood pressure measuring device 320. Drug-delivery device 330 is configured to automatically deliver a drug (e.g. dermally or transdermally) to the individual in response to the measured blood pressure(s).

System 300 may be suitably adapted to be used by an ambulatory individual to monitor and treat blood pressure excursions in real or near real time. Inflatable cuff 310 worn by the individual may be configured for manual or automatic inflation/deflation. An automatically inflating cuff 310 may be configured to automatically inflate and deflate more than once according to a predetermined schedule (e.g., once every one or two hours).

Drug-delivery device 330 may include or have access to a drug reservoir, depot, or store of suitable medication for treating blood pressure excursions or conditions of the individual.

In general drug delivery device 330 may utilize any know technique for drug delivery. Drug-delivery device 330 may, for example, include suitable electrical or electronic circuits to deliver the drug using iontophoresis, sonophoresis and/or electroporation. Other versions of drug-delivery device 330 may, for example, include suitable mechanisms to deliver the drug using abrasion, ablation, microneedles and/or perforation. Yet other versions of drug-delivery device 330 may, for example, include pneumatic or mechanical drivers to deliver the drug into the individual using microjets, and/or needleless injection.

System 300 may include a suitable controller 332 (e.g., a microprocessor based controller) configured to process blood pressure data and other data. Controller 332 may be configured to activate drug delivery device 330 to deliver prescribed amounts of the medication to treat the measured blood pressure excursions or conditions of the individual. Controller 332 may be configured to activate drug delivery device 330 to deliver the drug to the individual in response to one or more of, for example, current, average and/or cumulative blood pressure values, changes in blood pressure values and/or in projected blood pressure values. In a version of system 300, controller 332 may be configured to activate drug delivery device 330 to deliver the drug to the individual in response to parameters or characteristics of the blood pressure profile including pulse shape, and/or systolic/diastolic blood pressure values.

System 300 may further include a memory unit 334 to store blood pressure data and drug-delivery instructions. System 300 may also include an input/output communications interface 336. Controller 332 may, for example, communicate blood pressure values, system actions, and/or system status to, or receive drug delivery instructions from, an external source over wired or wireless links via input/output communications interface 336. Controller 332 and other electrical or electronic components of system 300 may be battery powered.

A version of system 300 may include an altitude-sensing device (e.g., an accelerometer) configured to determine an altitude of inflatable cuff 310 as worn by an individual during a blood pressure measurement. Controller 332 or other suitable processing circuitry included in system 300 may be configured to correct the blood pressure measurement for a relative height or altitude of inflatable cuff 310. For example, controller 332 may be configured to distinguish blood pressures measurements made when the individual' arm is lowered when sitting from those made when the arm is raised.

System 300 may be configured to deliver the prescribed drug to dynamically regulate the individual's blood pressure. System 300 may be configured to deliver the prescribed drug to lower or raise the individual's blood pressure(s), or to reach or maintain a target blood pressure or range. System 300 may also be configured to deliver to deliver a drug to treat a condition sensitive to a result and/or effect of the of the individual's blood pressure.

Figure 7:
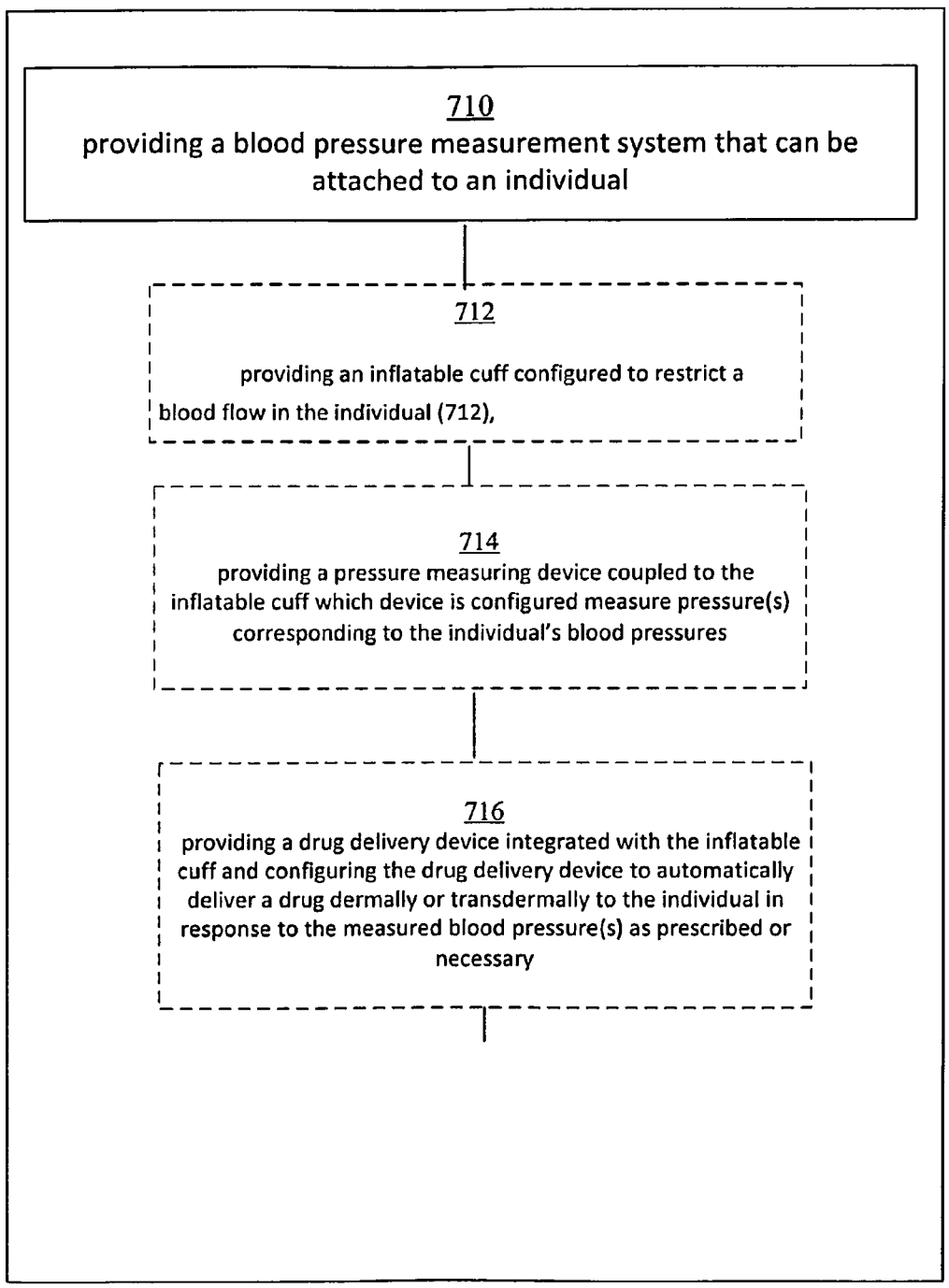
FIG. 7 is a flow diagram illustrating exemplary method for dynamically treating hypertension or other blood pressure incidents, in accordance with the principles of the solutions described herein.

FIGS. 5-7 show exemplary methods 500-700 for promptly treating blood pressure incidents in an individual on real time or near real time.

Method 500 (FIG. 5) includes providing a blood pressure monitoring unit having a built-in ultrasound sensor and a drug delivery device (510) that can be attached to an individual.

The blood pressure monitoring unit may be adapted to be attached to a skin portion of the individual and/or to be fully or partially implanted in the individual. The ultrasound sensor may be configured to locate a blood vessel in operation and make one or measurements of blood pressure in the located blood vessel.

Method 500 further includes making one or more blood pressure measurements of the individual with the ultrasound sensor in the attached unit (520), and using the attached drug-delivery device to dispense a drug to the individual in real time or near real time response to the measured blood pressure measurements as prescribed or appropriate to treat the individual's condition (530).

In method 500, providing a blood pressure monitoring unit having a built-in ultrasound sensor and a drug delivery device (510) may include providing a unit having a processing circuit configured to process blood pressure data and other data. Further, providing a blood pressure monitoring unit having a built-in ultrasound sensor and a drug delivery device (510) may include providing a drug-delivery device configured to dispense the drug to dynamically regulate the individual's blood pressure, to lower or raise the individual's blood pressure, reach or maintain a target blood pressure or range and/or to treat a condition sensitive to a result and/or effect of the individual's blood pressure.

Further in method 500, providing a blood pressure monitoring unit having a built-in ultrasound sensor and a drug delivery device (510) may include providing one of a broad angle sensor, a directed beam sensor, a bistatic sensor and a phased array ultrasound sensor. The sensor may be configured to make Doppler measurements of a blood flow in the individual by correlating blood velocity and pressure.

In a version of method 500, providing a blood pressure monitoring unit having a built-in ultrasound sensor and a drug delivery device (510) may include providing a sensor configured to measure dynamic changes in a blood vessel size or elasticity that are indicative of the blood pressure. In another or same version of method 500, providing a blood pressure monitoring unit having a built-in ultrasound sensor and a drug delivery device (510) may include providing a unit configured to apply sufficient energy to jostle blood in a blood vessel or the blood vessel itself and a sensor configured to measure the blood pressure response to the applied energy.

In a version of method 500, providing a blood pressure monitoring unit having a built-in ultrasound sensor and a drug delivery device (510) may include providing a drug-delivery device having one or one or more needles and/or, microjets for delivery of the drug to the individual and/or uses iontophoresis and/or, sonophoresis for delivery of the drug to the individual.

In method 500, using the attached drug-delivery device to dispense a drug to the individual in response to the measured blood pressure measurements as prescribed or appropriate to treat the individual's condition (530) may include, for example, dispensing the drug in response to current, average and/or cumulative blood pressure values, changes in blood pressure values and/or in projected blood pressure values, and/or in response to parameters or characteristics of the blood pressure profile including pulse shape, and/or systolic/diastolic blood pressure values.

Method 500 may further include providing the blood pressure monitoring unit with an input/output communications interface, a memory unit and/or a microprocessor. The memory unit may be configured to store one or more measured blood pressure values and/or drug-dispensation instructions. The microprocessor may be programmed to execute drug dispensing instructions, for example, based on blood pressure values. The input/output communications interface may be a signal or data interface configured to receive parameters relating drug dispensation requirements and blood pressure values, and/or other instructions from an external source. Method 500 may further include communicating blood pressure values, device actions and/or device status with an external point or source via the input/output communications interface.

A version of method 500 may further include providing an altitude sensing device (e.g., an accelerometer) configured to determine an altitude of the ultrasound sensor, and a circuit.

Method 600 (FIG. 6) includes providing a drug-delivery skin patch having a structurally integrated or built-in blood pressure sensor (610). The drug-delivery skin patch is adapted to be attached to a skin portion of an individual to needle-lessly deliver a drug dermally or transdermally to the individual. The built-in blood pressure sensor is configured to locate a blood vessel in operation and make one or measurements of blood pressure in the located blood vessel.

Method 600 further includes configuring the skin patch to needle-lessly deliver a drug dermally or transdermally to the individual as may be prescribed or appropriate in response to blood pressure determinations with the built-in blood pressure sensor (620).

In method 600 includes providing a drug-delivery skin patch having a structurally integrated or built-in blood pressure sensor (610) may include providing a mechanical, optical, ultrasonic, and/or electric blood pressure sensor. The ultrasonic sensor may be one of a broad angle, a directed, a bistatic and/or a phased array ultrasonic sensor. The ultrasonic sensor may be configured to make Doppler measurements of a blood flow in the individual by correlating blood velocity and pressure.

Further, in method 600 providing a drug-delivery skin patch having a structurally integrated or built-in blood pressure sensor (610) may include providing a blood pressure sensor that is configured to measure dynamic changes in a blood vessel size or elasticity that are indicative of the blood pressure. The blood pressure sensor may be configured to apply sufficient energy to jostle blood in a blood vessel or the blood vessel itself and to measure a blood pressure response to applied energy.

In method 600 configuring the skin patch to needle-lessly deliver a drug dermally or transdermally to the individual as may be prescribed or appropriate in response to blood pressure determinations with the built-in blood pressure sensor (620) may providing electrical circuits and/or pneumatic or mechanical drivers to deliver the drug using iontophoresis, electroporation, sonophoresis, via microjets, and/or needle-less injection.

Further, in method 600 configuring the skin patch may include configuring the skin patch to deliver the drug in response to current, average and/or cumulative blood pressure values, in response to trends in blood pressure values and/or to projected blood pressure values, and/or in response to parameters or characteristics of the blood pressure profile including pulse shape, and/or systolic/diastolic blood pressure values.

Method 600 may further include providing a processing circuit (e.g., a microprocessor) and an input/output communications interface in the skin patch. The processing circuit may be configured to process blood pressure data and other data. The processing circuit may be further configured and to communicate blood pressure values, system actions and/or system status with an external source or point via the input/output communications interface.

Method 600 may also include providing an altitude sensing device (e.g. an accelerometer) configured to determine an altitude of the blood pressure sensor, and configuring the processing circuit or other circuits to correct a blood pressure measurement for a relative height of the sensor.

Method 600 may further include configuring the skin patch to deliver the drug to dynamically regulate the individual's blood pressure, to lower or raise the individual's blood pressure, to reach or maintain a target blood pressure or range and/or to treat a condition sensitive to a result and/or effect of the individual's blood pressure.

Method 700 (FIG. 7) includes providing a blood pressure measurement system that can be attached to an individual (710). Providing a blood pressure measurement system that can be attached to an individual (710) includes providing an inflatable cuff configured to restrict a blood flow in the individual (712), and providing a pressure measuring device coupled to the inflatable cuff which device is configured measure pressure(s) corresponding to the individual's blood pressures (714). Providing a blood pressure measurement system that can be attached to an individual (710) further includes providing a drug delivery device integrated with the inflatable cuff and configuring the drug delivery device to automatically deliver a drug dermally or transdermally to the individual in response to the measured blood pressure(s) as prescribed or necessary (716).

In method 700, the inflatable cuff may be configured for may be for manual or automatic inflation. The inflatable cuff may, for example, be configured to automatically inflate and deflate more than once according to a predetermined schedule. Further, the pressure measuring device may include a mechanical, audio, optical, and/or electric sensor.

Further in method 700, providing a drug delivery device integrated with the inflatable cuff may include providing the drug delivery device with electrical circuits and other pneumatic or mechanical mechanisms or drivers to deliver the drug using one or more of iontophoresis, sonophoresis and/or electroporation, abrasion, ablation, microneedles, perforation, microjets, and/or needle-less injection.

Method 700 may further include configuring the drug delivery device to deliver the drug in response to current, average and/or cumulative blood pressure values, changes in blood pressure values and/or in projected blood pressure values, and/or in response to parameters or characteristics of the blood pressure profile including pulse shape, and/or systolic/diastolic blood pressure values.

Like method 600, method 700 may also include a processing circuit configured to process blood pressure data and other data. Method 700 may also further include providing an input/output communications interface and configuring the blood pressure measurement system to communicate blood pressure values, system actions, and/or system status with an external point via the input/output communications interface.

Method 700 may also include providing an altitude sensing device (e.g. an accelerometer) configured to determine an altitude of the pressure measuring device, and configuring the processing circuit or other circuits to correct a blood pressure measurement for a relative height of the sensor.

Method 600 may further include configuring the drug delivery device to deliver the drug to dynamically regulate the individual's blood pressure, to lower or raise the individual's blood pressure, to reach or maintain a target blood pressure or range and/or to treat a condition sensitive to a result and/or effect of the individual's blood pressure.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures. Electronic circuitry, for example, may have one or more paths of electrical current constructed and arranged to implement various functions as described herein. In some implementations, one or more media may be configured to bear a device-detectable implementation when such media hold or transmit a device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled/implemented/translated/ converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electromagnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into an image processing system. Those having skill in the art will recognize that a typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Those skilled in the art will recognize that at least a portion of the devices and/or processes described herein can be integrated into a mote system. Those having skill in the art will recognize that a typical mote system generally includes one or more memories such as volatile or non-volatile memories, processors such as microprocessors or digital signal processors, computational entities such as operating systems, user interfaces, drivers, sensors, actuators, applications programs, one or more interaction devices (e.g., an antenna USB ports, acoustic ports, etc.), control systems including feedback loops and control motors (e.g., feedback for sensing or estimating position and/or velocity; control motors for moving and/or adjusting components and/or quantities). A mote system may be implemented utilizing suitable components, such as those found in mote computing/communication systems. Specific examples of such components entail such as Intel Corporation's and/or Crossbow Corporation's mote components and supporting hardware, software, and/or firmware.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory.

Further, implementation of at least part of a system for performing a method in one territory does not preclude use of the system in another territory.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Although user is shown/described herein as a single illustrated figure, those skilled in the art will appreciate that user may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., " a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., " a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A blood pressure measurement system, comprising:
   an inflatable cuff configured to restrict a blood flow in an individual;
   a pressure measuring device coupled to the inflatable cuff to measure pressure(s) corresponding to the individual's diastolic and/or systolic blood pressures; and
   a drug delivery device integrated with the inflatable cuff, wherein the drug delivery device is configured to automatically deliver a drug dermally or transdermally to the individual in response to at least one of projected or cumulative blood pressure values determined from the measured blood pressure(s).

2. The system of claim 1, wherein the inflatable cuff is configured for manual or automatic inflation.

3. The system of claim 1, wherein the inflatable cuff is configured to automatically inflate and deflate more than once according to a predetermined schedule.

4. The system of claim 1, wherein the drug delivery device includes electrical circuits to deliver the drug using iontophoresis, sonophoresis and/or electroporation.

5. The system of claim 1, wherein the drug delivery device includes mechanisms to deliver the drug using abrasion, ablation, microneedles and/or perforation.

6. The system of claim 1, wherein the drug delivery device includes drivers to deliver the drug using microjets, and/or needle-less injection.

7. The system of claim 1, wherein the drug delivery device is configured to deliver the drug in response to the pulse shape of the blood pressure profile.

8. The system of claim 1, further comprising an input/output communications interface.

9. The system of claim 8, further configured to communicate blood pressure values, system actions, and/or system status with an external point via the input/output communications interface.

10. The system of claim 8, configured to receive drug delivery instructions from an external source via the input/output communications interface.

11. The system of claim 1, further comprising an altitude sensing device configured to determine an altitude of the inflatable cuff.

12. The system of claim 11, wherein the altitude sensing device includes an accelerometer.

13. The system of claim 11, comprising:
    a microprocessor based controller configured to correct the measured blood pressure(s) for the relative altitude of the inflatable cuff and to activate the drug delivery device to deliver the drug to the individual in response to the corrected measured blood pressure(s).

14. The system of claim 1, further comprising a circuit configured to correct a blood pressure measurement for a relative height of the sensor.

15. The system of claim 1, further comprising a processing circuit configured to process blood pressure data and other data.

16. The system of claim 1, wherein the drug delivery device is configured to deliver the drug to reach or maintain a target blood pressure or range.

17. The system of claim 1, wherein the pressure measuring device includes an ultrasound sensor.

18. The system of claim 17, wherein the ultrasound sensor includes a broad angle sensor.

19. The system of claim 17, wherein the ultrasound sensor includes at least one of a directed beam sensor, a bistatic sensor, and a phased array ultrasound sensor.

20. The system of claim 1, wherein the pressure measuring device includes a mechanical sensor.

21. The system of claim 1, wherein the pressure measuring device includes an audio sensor.

22. The system of claim 1, wherein the pressure measuring device includes an optical sensor.

23. The system of claim 1, wherein the pressure measuring device includes an electrical sensor.

24. The system of claim 1, comprising a memory unit for storing blood pressure values or drug delivery instructions.

25. A method for treating a blood pressure condition of an individual, comprising:
   providing a blood pressure measurement system that can be attached to an individual,
   wherein the blood pressure measurement system has an inflatable cuff configured to restrict a blood flow in the individual;
   wherein a pressure measuring device is coupled to the inflatable cuff to measure a pressure corresponding to the individual's blood pressure,
   wherein a drug delivery device is integrated with or built-in to the inflatable cuff, and
   wherein the drug delivery device is configured to automatically deliver a drug dermally or transdermally to the individual in response to at least one of projected or cumulative blood pressure values determined from the measured blood pressure(s).

26. A method for treating a blood pressure condition of an individual, comprising:
   automatically inflating an inflatable cuff forming a part of a blood pressure measurement system attached to an individual to restrict a blood flow in the individual;
   measuring a pressure corresponding to the individual's blood pressure with a pressure measuring device coupled to the inflatable cuff;
   determining at least one of a projected or cumulative blood pressure value based in part on the measured pressure; and
   automatically delivering a drug dermally or transdermally to the individual with a drug delivery device integrated with or built-in to the inflatable cuff in response to the at least one determined projected or cumulative blood pressure value.

27. The method of claim 26, comprising:
   determining a relative altitude of the inflatable cuff with an accelerometer forming a part of the blood pressure measurement system; and
   correcting the measured blood pressure(s) for the relative altitude of the inflatable cuff.

28. The method of claim 26, comprising attaching the blood pressure measurement system to a skin portion of the individual.

29. The method of claim 26, comprising automatically inflating and deflating the inflatable cuff more than once according to a predetermined schedule.

30. The method of claim 26, comprising receiving parameters relating to drug dispensation requirements and blood pressure values and/or other instructions from an external source via an input/output communications interface, wherein the input/output communications interface is a part of the blood pressure measurement system.

31. The method of claim 26, comprising communicating blood pressure values, device actions and/or device status to an external point via an input/output communications interface, wherein the input/output communications interface is a part of the blood pressure measurement system.

32. The method of claim 26, wherein measuring the pressure corresponding to the individual's blood pressure with the pressure measuring device includes making one or more ultrasonic measurements of the individual's blood pressure.

33. The method of claim 32, wherein making one or more ultrasonic measurements of the individual's blood pressure includes making Doppler measurements of a blood flow in the individual by correlating blood velocity and pressure.

34. The method of claim 26, comprising locating a blood vessel and making one or more measurements of blood pressure in the located blood vessel.

35. The method of claim 34, comprising measuring dynamic changes in blood vessel size or elasticity that are indicative of blood pressure.

36. The method of claim 35, comprising applying sufficient energy to jostle blood in the blood vessel or walls of the blood vessel and measure a blood pressure response to the applied energy.

37. The method of claim 26, comprising delivering the drug in response to average blood pressure values.

38. The method of claim 26, comprising delivering the drug in response to cumulative blood pressure values.

39. The method of claim 26, comprising delivering the drug in response to projected blood pressure values.

40. The method of claim 26, comprising delivering the drug in response to a blood pressure profile pulse shape.

* * * * *

UNITED STATES PATENT AND TRADEMARK OFFICE
CERTIFICATE OF CORRECTION

| | | |
|---|---|---|
| PATENT NO. | : 8,702,614 B2 | Page 1 of 1 |
| APPLICATION NO. | : 13/373364 | |
| DATED | : April 22, 2014 | |
| INVENTOR(S) | : Baym et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 10 days.

Signed and Sealed this
Eleventh Day of August, 2015

Michelle K. Lee
*Director of the United States Patent and Trademark Office*